United States Patent [19]

Vinopal

[11] 4,289,037
[45] Sep. 15, 1981

[54] METHOD OF STRESS GRADING TIMBER, AND MACHINE FOR STRESS GRADING TIMBER

[75] Inventor: George W. Vinopal, Pretoria, South Africa

[73] Assignee: South African Inventions Development Corporation, Pretoria, South Africa

[21] Appl. No.: 116,433

[22] Filed: Jan. 29, 1980

[30] Foreign Application Priority Data

Feb. 7, 1979 [ZA] South Africa ............... 79/0530

[51] Int. Cl.³ ............................................. G01N 3/32
[52] U.S. Cl. ........................................ 73/808; 73/811; 73/812
[58] Field of Search ............... 73/808, 811, 812; 204/517, 518

[56] References Cited

U.S. PATENT DOCUMENTS 3,196,672 7/1965 Keller ............................ 73/812

FOREIGN PATENT DOCUMENTS 1056167 8/1965 United Kingdom.
1322953 10/1970 United Kingdom.
1466741 3/1973 United Kingdom.

Primary Examiner—Anthony V. Ciarlante
Attorney, Agent, or Firm—Ladas & Parry

[57] ABSTRACT

The invention provides a method of stress grading timber, and a timber stress grading machine. The method and machine involve continuously moving a length of timber and stressing the moving length by applying a transverse load thereto. The length is supported by two supports between which the load is applied and the load causes a deflection of the timber length. The load and/or deflection are measured and the moving length is stressed differently by thereafter applying a different load to the timber length at the same position while supported in the same fashion to obtain a different deflection. The different load and/or deflection are measured and the original load and original deflection are related to the different load and different deflection according to predetermined criteria, thereby to grade the timber length. The machine provides means for carrying out the method.

14 Claims, 1 Drawing Figure

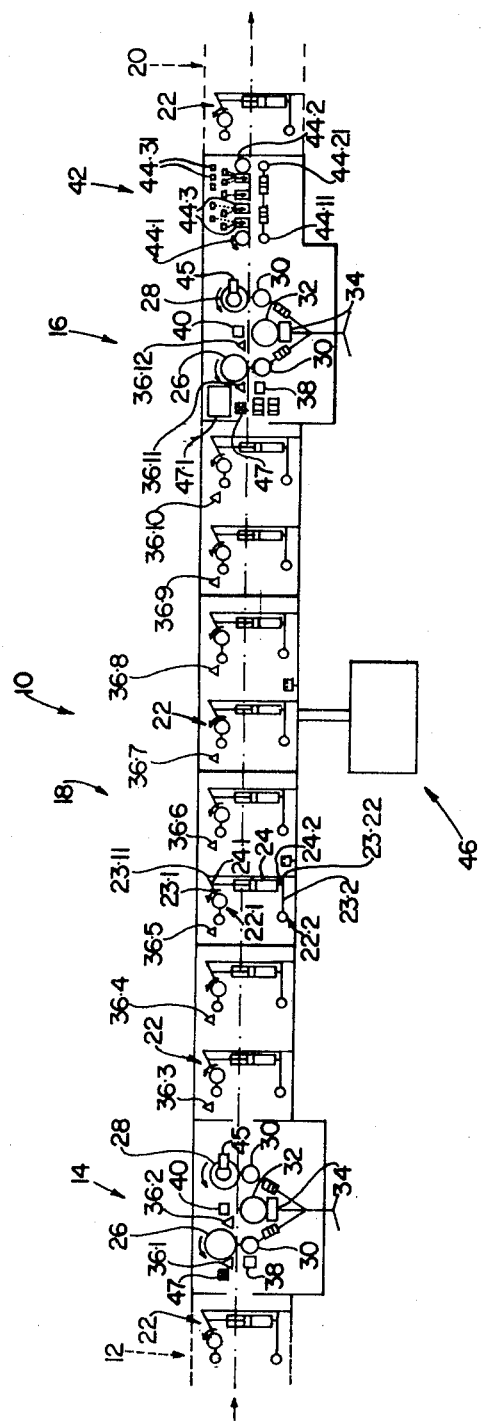

METHOD OF STRESS GRADING TIMBER, AND MACHINE FOR STRESS GRADING TIMBER

This invention relates to a method of stress grading timber, and to a machine for stress grading timber.

By "stress grading timber" is meant stressing the timber by applying a load in a transverse direction to a length of timber, and relating the load applied to the deflection of the timber caused by the load, thereby to assign the timber to one of two or more, more or less arbitrary, grades, depending on the stiffness of the timber, i.e. the deflection obtained for a particular load.

According to the invention a method of stress grading timber comprises:

continuously moving a length of timber;

stressing the moving length of timber by applying a transverse load thereto, the length being supported by two supports between which the load is applied and the load causing a deflection of the timber length;

measuring the load and/or the deflection;

thereafter stressing the moving length differently by applying a different load to the timber length at the same position while supported in the same fashion to obtain a different deflection;

measuring the different load and/or the different deflection; and relating the original load and original deflection to the different load and different deflection according to predetermined criteria, thereby to grade the timber length.

It will be appreciated that using differences in loads and deflections provides an important advantage of eliminating the effects of bow on the readings, as differences in loads related to differences in deflections can be used to grade the timber length.

The method may include applying the original load and the different load from the same side of the timber length, so that the length is in each case deflected in the same direction. The timber length may be freely supported as a simple beam during each stressing thereof, the length being substantially unconstrained during the stressing except by the load and the two supports between which the load is applied. Thus, during stressing, the board is supported essentially only by two supports which are spaced lengthwise relative to the timber length and which are located on one side of the timber length, the load being applied to the opposite side of the timber length, at a position, lengthwise relative to the timber length, between said supports. The load is conveniently applied midway between the supports.

The original and different loads, i.e. the original and different stressings, may be applied to the length of timber at a plurality of spaced positions spaced lengthwise along the timber length. This is conveniently effected by in each case advancing the timber length past the supports, and stressing it at said plurality of positions as it is so advanced, thereby enabling the minimum stiffness of the timber length to be determined, and also the position lengthwise along said timber length where it is of minimum stiffness. This enables the positions of zones of weakness such as knots in said timber length to be identified. The spaced positions should thus be as close together as is reasonably practicable.

As mentioned above, the length is conveniently supported as a simple beam with the load being applied midway between the supports. This is so that the maximum deflection is obtained for a particular loading, or so that the minimum loading is obtained for a particular deflection, to obtain the maximum sensitivity of the stressing for the most accurate results. The effects of imperfections such as knots are magnified when the loading takes place directly on such imperfections. The spacing between the positions should thus be so small that no significant imperfection will escape being loaded more or less directly, so that it is identified and so that the reduced stiffness caused by the imperfection is properly measured. It has been found that a suitable spacing is of the order of 25–60 mm for practical purposes, being preferably less than about 50 mm.

The span between each pair of supports between which the timber length is loaded may be less than 600 mm, and for practical purposes it is preferably in the range of 300–500 mm. The effect of imperfections is magnified, and sensitivity of grading to imperfections and to determining their location is increased, if the span between the supports is kept as low as practicably possible, the above magnitudes of span having been found by the applicant to be suitable. The use of the lowest practicable span between supports during loading to magnify the effect of imperfections on stiffness, requires increased sensitivity of measurement, as deflections caused by loading become smaller together with the reduction in span. It is thus preferred, in measuring the stiffness of the board, to measure the loads which cause fixed deflections, rather than the deflections caused by fixed loads.

Each original load may be applied at one location, the timber length then being moved to another location where each different load is applied. Thus, two pairs of supports may be provided at different locations provided by two different work stations, the timber length being stressed at one work station, and moved to the other work station, where the different stress is applied. Thus the method may comprise advancing the timber length past said locations, and stressing the timber length at the same positions along its length at each of the locations. At each work station or location where the timber length is stressed, the spacing between the positions along the length of the timber length where it is stressed are preferably the same, and the positions themselves are preferably the same, so that the positions where the different loads are applied to the timber length are the same positions as, and coincide with, the positions where the load was applied at the first location during the original stressing.

The timber length will be advanced continuously past said locations, and may be moved continuously from the first location to the second location. If the timber length is a board, it preferably has its major faces vertical, and is stressed normal to its major faces, the load being applied in a horizontal direction to one of the major faces of the board.

The method may include measuring the thickness of the timber length, and using said thickness in conjunction with the loadings and deflections, to grade the length, the thickness being used for example in determining the modulus of elasticity of the length.

The thickness of the board may be measured before the first stressing, and its actual thickness can be used, optionally, in conjunction with other factors such as timber type, the width of the board and the like, to determine a suitable original stressing to which the length is subjected. Instead, as mentioned above, the thickness measured need only be used to obtain the modulus of elasticity, and the nominal thickness of the board may be used to fix the original stressing.

In this regard "thickness" means the cross sectional dimension of the timber length transverse to the timber length, in the direction in which the load of the stressing is applied. "Width" is correspondingly the cross sectional dimension of the length, transverse to its lengthwise direction, normal to the direction in which thickness is measured. For a timber length in the form of a board which is loaded on one of its major faces, the width will thus be the dimension of the board transverse to its length, across its major faces, and the thickness will be the spacing between its major faces.

When the timber length is advanced past the supports, for example when it is advanced past the first and second locations at the work stations, the method may include measuring its thickness at a plurality of positions spaced along its length, thereby to obtain an indication of the average thickness of the timber length, for better prediction of stiffness and grading. The spacings between the positions at which thickness is measured conveniently are the same as the spacings between the positions where the board is stressed.

Conveniently, when determining the stiffness of the timber length at a particular position, the average thickness of the timber length at and on opposite sides of the position where it is loaded may be used to calculate its stiffness. The distance along the board over which this average thickness is taken into account for measuring stiffness at a particular position, may comprise, say, two or three load spacings on opposite sides of the position in question. Thus if the board is loaded every 50 mm along its length, its thickness averaged over a length of 200–300 mm may be used to calculate stiffness, the loading applied to the centre of the portion over which thickness is averaged.

The deflection obtained from each original stressing may be used to predict a suitable non-destructive load to which the length is to be subjected during the corresponding different stressing. Thus the method may comprise using the load applied to stress the length and the deflection obtained thereby during the original stressing, together with such factors as the thickness, cross section and type of timber of the timber length, to predict an increased different stressing to which the length can safely be subjected, said predicted increased stressing being applied during the subsequent different stressing. Thus the original stressing is preferably at low values of load and deflection, and the subsequent different stressing is then carried out at the highest non-destructive stressing which the timber length is predicted as being capable of withstanding, thereby to achieve the largest differences between the loads in the two stressings and the largest differences in deflections in the two stressings, for enhanced accuracy.

The method may be computer-controlled, so that all the method steps are automatically carried out in a predetermined sequence. Thus the advancement of the timber length past said locations may be monitored by photo-electric cells or similar detection devices, operative via the computer to control the measurement of thickness, to control the degree of stressing in terms of load applied and deflection obtained, and to control the physical movement of the timber lengths.

To permit measurement of load rather than deflection, as mentioned above, each timber length is preferably advanced at a constant deflection past each of said locations, variations in load being measured at said locations by load cells such as load transducers.

The method may comprise using the computer automatically to grade the timber lengths, in accordance with their predicted strengths arising from the stressings applied at the said locations, and the method may comprise marking said boards accordingly, and marking and identifying boards having imperfections, the locations of the imperfections being identified and boards capable profitably of being sawn where the imperfections are located towards the ends thereof, also being identified.

Further according to the invention a timber stress grading machine comprises:

means for continuously moving a length of timber.

means for stressing the moving length of timber by applying a transverse load thereto, the length being supported by two supports between which the load is applied, to cause a deflection of the timber length;

means for measuring said load and/or deflection;

means for then stressing the moving length differently at the same position while supported in the same fashion to obtain a different deflection;

means for measuring the different load and/or the different deflection; and means for relating the original load and original deflection to said different load and different deflection according to predetermined criteria, thereby to grade the timber length.

The means for applying the original load and the different load to the timber length may be arranged to act on the same side of the timber length, so that the length is in each case deflected in the same direction. The supports in each case may act freely to support the length as a simple beam during stressing thereof, so that the length is substantially unconstrained during stressing except by the load and the two supports between which the load is applied.

The machine may be adapted to apply the original load and the different load to the length of timber at a plurality of spaced positions spaced lengthwise along the timber length.

The span between each pair of supports between which the length is loaded may be less than 600 mm, preferably 300–500 mm as described above.

The means for originally stressing the timber length is conveniently at one location, the means for differently stressing the length being at a different location and the machine including means for moving the timber length from the one location to the different location. However, it will be appreciated that the means for the original and different stressings may be the same means, at a single location, the timber length being moved past said location and stressed twice in succession.

The machine may include means for measuring the thickness of the timber length, the means for relating the original load and deflection to the different load and deflection being adapted to use the thickness measurement(s) so obtained, in the grading of the timber length.

The means for stressing the timber length differently may be responsive to the load and deflection of the original stressing, being adapted to provide said different load with a magnitude which depends on said original load and deflection.

The means for moving the timber length from the one location to the other may be adapted to move said length continuously.

When the machine is adapted to stress the timber lengths at different locations, as described above, the locations will each be at work stations having the supports for the timber length and the means for applying a load to the timber length arranged in substantially identical fashion. Thus, as described above, the spacing between the supports and the position of the means for applying the load between the supports will be the same at each work station, and the work stations will preferably be adapted to apply the load in the same direction at each work station.

The means for moving the timber lengths may comprise pairs of laterally spaced rollers, the pairs being spaced in series along the path which the timber lengths follow through the machine, said rollers conveniently having upright axes and being provided in the work stations, on a feed table leading to the first i.e. original work station, on an interconnecting table interconnecting the work stations, and on an outfeed table leading from the second i.e. different work station. Thus, the supports against which the timber lengths are stressed may be support rollers, and the means for applying the transverse load between said support rollers may also comprise a roller. Said rollers may further include, at each work station, a drive roller which conveniently is one of the support rollers, and may comprise, opposite each said support roller, a biassing roller whereby the timber lengths are biassed against the drive roller, said biassing roller conveniently being a pressure roller biassed by a fluid such as pneumatic fluid, under pressure.

As each timber length moves through the machine it will conveniently be held in the same attitude, and the load will be applied to the timber length from the same side of the timber length in each work station so that the length is in each case deflected in the same direction. The support rollers will support the timber length preferably as a simple beam. The surface along which the timber length moves in each work station will have a negligible effect on the accuracy of the stressing. When the timber length moves continuously through the machine, it is possible to apply the load continuously along the timber length as it moves, and to measure the load and deflection at spaced time intervals, corresponding to spaced positions lengthwise along the timber length.

The machine may include means, such as a plurality of photo-electric cells, spaced along the path followed by the timber length through the machine, to detect and monitor progress of timber lengths through the machine. The machine may further include, at the first work station, the means for measuring thickness, which may be a thickness sensor which may comprise a transducer, whereby the thicknesses of timber lengths passing through the machine are measured.

At each work station the means for measuring the load applied may be a load cell, such as a load transducer, for measuring the load applied to each timber length as it is stressed in said work station.

Each work station will also include means for displacing the means for applying the load to the timber length, and means for measuring said displacement and hence the deflection of the timber length.

The means for advancing the timber lengths at each work station may include an impulse generator, and the machine may include means for marking information on the timber lengths as they pass through the machine.

Finally, the machine may include a control unit, such as a computer and memory system, for controlling advancement and movement of the timber lengths, and for controlling the stressing of the timber lengths as they are advanced through the work stations, in relation to the deflection and load applied thereto. This computer and memory system will act as the means for relating the original load and the original deflection to the different load and different deflection, according to the predetermined criteria, to grade the timber length. For each timber length it can determine the stiffness at any position at which it is measured on the timber length, and can determine the minimum stiffness and position thereof, and the clear stiffness by averaging a certain percentage or proportion of the stiffness measured, being the highest stiffness measured. This "clear" stiffness is the stiffness at positions along the timber length where it is clear of imperfections such as knots. When the thickness is measured and is taken into account by the computer in relating the original load and deflection to the different load and deflection, for each position where stiffness is measured, the computer can use the average thickness of the timber length for a short distance on opposite sides of the position where stiffness is measured, as described above with reference to the method aspect of the present invention.

The computer and memory system will be connected to and responsive to the photo-electric cells, to monitor the progress of each timber length along its path through the machine, for controlling the stressing of the timber lengths and thickness measurement thereof, in response to said progress. The computer and memory system may also be connected to and responsive to the thickness sensor, for controlling the amount of stressing applied to the timber lengths at the first work station, in response to changes in thickness between timber lengths passing through the machine; and said computer and memory system may be connected to the impulse generator of the first work station for operating the thickness sensor and for controlling the load applying means, so that the thickness of each timber length is sensed and so that each timber length is loaded at regular intervals along its length as it passes through the first work station, conveniently at the same equally spaced intervals. Likewise, said system may be responsive to the impulse generator of the second work station, for controlling the associated load applying means, to load such timber length at the second work station at regular intervals along its length, preferably at the same positions as it was loaded in the first work station.

Finally, the computer and memory system may be connected to and responsive to the load cell and displacement sensor of the first work station, thereby to control the stressing applied to each timber length at the second work station, in response to the displacement and load applied to that timber length at the first work station; and the system may be connected to the displacement sensor and load cell of the second work station, for comparing the load and displacement at the second work station with the load and displacement applied to the same timber length at the first work station, and for performing the necessary calculations according to the predetermined criteria to grade the timber length; and said system may be connected to an information marking mechanism thereby to provide for the marking of grading and similar information on each graded timber length.

The invention will now be described, by way of example, with reference to the accompanying diagrammatic drawing, in which the single FIGURE shows a plan view of a timber stress grading machine in accordance with the invention.

In the drawing, reference numeral 10 generally designates a timber stress grading machine in accordance with the invention. The machine comprises an infeed table 12, a first work station generally designated 14, a second work station generally designated 16, an interconnecting table 18 connecting the station 14 with the station 16, and an outfeed table 20 from the station 16. The machine 10 is suitable for stress grading timber lengths in the form of sawn or planed wooden boards. The tables 12, 18 and 20 are horizontal, and are adapted to move boards along a predetermined path through the machine 10, by means of holding rollers 22. The rollers 22 (22.1 and 22.2 as described hereunder) are arranged in pairs spaced longitudinally along the tables, the rollers of each pair being spaced laterally, and straddling the path along which the boards move.

One of the rollers of each pair, marked 22.1, is a double roller and is driven, the other, marked 22.2, being an idler roller. The double roller 22.1 is mounted on a lever 23.1 pivotally mounted at 23.11 about an upwardly extending axis. The roller 22.2 in each case is mounted on a lever 23.2, likewise pivotally connected about an upwardly extending axis at 23.22. The levers 23.1, 23.2 are interconnected by a pneumatic piston and cylinder assembly 24, which is connected to the lever 23.1 at 24.1 about an upwardly extending pivotal axis, and to the lever 23.2 at 24.2 about an upwardly extending pivotal axis. Extension of the assembly 24 moves the rollers 22.1, 22.2 away from each other and contraction of said assembly moves said rollers together, thereby to grip a board therebetween. The holding rollers of the table 18 are drivingly connected to the drive of the first work station 14 (described hereunder) by a V-belt drive (not shown). The holding rollers 22 of the infeed table 12 and outfeed table 20 may be similarly connected to the drives respectively of the first work station 14 or the second work station 16, or may be otherwise suitably driven.

Each work station 14, 16 comprises a pair of support rollers, namely a drive roller 26 and an idler support roller 28, which are spaced by 500 mm from each other in the direction of the path followed by boards through the machine. Each support roller 26, 28 is provided, opposed thereto and on the opposite side of said path, with a pneumatically operated biassing or pressure roller 30 adapted to hold a board passing through the machine against the associated support roller 26, 28. Each work station is provided with load applying means in the form of an idler roller 32 mounted on a pneumatic displacement regulator 34 whereby it is transversely, i.e. laterally, displaceable, relative to the path taken by boards through the machine. The regulator 34 includes a hydraulic piston and cylinder assembly for damping its motion.

Said idler rollers 32 are each provided with a load tranducer associated with their displacement regulators 34 for measuring the load applied by the roller 32 to a board spanning the associated rollers 26, 28.

A plurality of photo-electric cells, for sensing and monitoring the progress of boards through the machine, is provided in series along the machine. The photo-electric cells are designated (for the work stations 14, 16 and table 18) 36.1 to 36.12. Cell 36.1 is located immediately upstream of the support roller 26 of station 14 and downstream of the rollers 22 of the table 12, cell 36.2 being located upstream of the roller 32 and downstream of the roller 26 of the table 14.

Cells 36.3 to 36.10 are spaced in series from the upstream end of the table 18 to the downstream end thereof, each cell being located slightly upstream from an associated pair of rollers 22 on the table 18. Cells 36.11 and 36.12 are located in the station 16, at the same positions respectively as are occupied by the cells 36.1 and 36.2 in the station 14. Similar cells (not shown) can be provided on the tables 12 and 20, upstream of the pairs of rollers 22 thereon, in the same fashion as for the table 18, for the same purpose as described hereunder for table 18.

The station 14 is provided with a thickness sensor 38 comprising a transducer immediately upstream of and associated with upstream roller 30, for sensing the thickness of boards travelling through the machine. The stations 14, 16 are also each provided with a displacement sensor 40 comprising a tranducer, for sensing displacement of the roller 32 of the associated work station.

A marking mechanism is provided immediately downstream of the work station 16, in the form of a printing table, generally designated 42. On the printing table 42 are provided, spaced longitudinally along the path taken by a timber length through the machine, a drive roller 44.1 and, downstream thereof, an idler roller 44.2. Opposite the rollers 44.1 and 44.2 are pneumatically operated pressure rollers 44.11 and 44.21 respectively. Between the rollers 44.1 and 44.2 are a plurality of stampers 44.3 which act as marking mechanisms for marking the timber length grade, and other desired information on each timber length. They are operated by double-acting pneumatic piston and cylinder mechanisms 44.31. The table 42 is mounted so that it is easily and lightly movable laterally relative to the path through the machine taken by the timber lengths, and so that its influence on the deflection of a timber length moving out from the second work station 16 and still being deflected by said second work station 16, is negligible and does not influence the accuracy of results obtained from the second work station 16.

The displacement sensors 40 are mounted to be movable with the associated rollers 32. The rollers 28 are provided with impulse generators 45, the function of which will be described hereunder.

The machine 10 also includes a computer and memory system, in the form of a unit, generally designated 46.

The work stations are respectively provided with hydraulic motors 47 which are connected to a hydraulic power source 47.1 located at the second work station 16, and the machine further includes various types of anciliary electrical and service equipment (not shown) including means for adjusting the gap between the rollers 26, 28 and their associated rollers 30 when boards are not between them; comparators; selectors; switches; display units; relays, pilot lights, analogue scales and the like.

The computer and the information storage unit 46 is operatively connected to the photo-electric cells on the tables 12 and 20 and to the cells 36.1 to 36.12, to the thickness sensor 38, to the load transducers at 34 associated with the rollers 32, and to the displacement sensors 40, to receive data therefrom, and to store such data temporarily, when necessary. The unit 46 is also operatively connected to the displacement regulators 34, and to the marking mechanisms to the table 42, to control operation thereof in response to data received by the unit 46. The unit 46 is also connected to the drive motors 47 and thence to the rollers 22 and 26, to control operation thereof in response to data received by the unit.

Typically, the machine 10 is suitable for grading rough sawn or preferably planed timber boards of a thickness in the range 20-55 mm, width in the range 75-315 mm, and length in the range 1200-7900 mm, the boards passing through the machine at a speed between 25 and 150 meters a minute. For boards of this nature, the suitable span between the support rollers 26 and 28 in the respective stations 14 and 16 is, as mentioned above, 500 mm. In use, the machine 10 is set up to grade boards of a particular nominal width and thickness, and timber of a particular species, and of a specified minimum length, the unit 46 being preprogrammed accordingly, and the drive motors 47 being set to move the boards through the installation at a desired appropriate grading speed. The programming will include predetermined stiffness limits for grades of timber; information regarding safe or non-destructive bending stresses to which boards of the type being tested can be subjected; the depth of indentation by the various rollers of the board surfaces anticipated, caused by pressure of the rollers on the timber; the moisture content of the timber; changes in span and neutral axis datum line of the timber caused by deflection thereof during loading, etc.

In use, boards to be graded are fed sequentially into the machine, supported on edge on the table 12, the leading end of each board being fed in turn between the rollers 22 on said table 12.

When the leading end of the board is sensed by the cells 36 associated with the pairs of rollers 22 on the table 12 these rollers are activated by the unit 46 so that the rollers 22 of each pair move towards each other, to grip the board between them. At the same time the rollers 22 are driven to move the board along the table 12 and to advance the board into the work station 14. To move the board and hold it, only the two pairs of rollers nearest the leading edge of the board need be activated at any one time, the pairs of rollers 22 upsteam thereof being released in sequence as the board moves along.

When the leading end of the board is sensed by the cell 36.1 the impulse generator 45 on the roller 28 of the work station 14 is activated to generate pulses which enable the thickness sensor 38 and the load transducer associated with the associated roller 32 to take appropriate measurements at spaced positions along the length of the board as described hereunder. The photo-electric cell 36.1 also activates the displacement regulator 34 associated with the roller 32 of the work station 14, which regulator 34 starts moving the associated roller 32 across the path of the board towards the rollers 26 and 28.

Simultaneously the load transducer associated with the roller 32 in the work station 14 is activated, and it starts to transmit force values to the unit 46 as soon as the leading end of the board comes into contact with the roller 32.

When the leading end of the board operates the photo-electric cell 36.2, the thickness sensor 38 associated with the roller 30 transmits a measurement of the thickness of the board to the unit 46.

The unit 46, from the actual thickness of the board measured by the thickness sensor 38, can, if desired, determine from pre-programmed information as to the safe bending stress for the timber in question, a suitable deflection for stressing the board between the rollers 26 and 28 on the one hand, and 32 on the other hand. The unit simultaneously computes what force must be applied by the roller 32 to the board to locate the roller 32 at a displacement from its starting position which corresponds to this deflection.

The roller 32 at this stage is still being moved towards the rollers 26 and 28 by the displacement regulator 34, and the associated load transducer is continuing to transmit measurements of the force applied to the board to the unit 46, for comparison with said computed value. As soon as the force reaches this computed value, the displacement regulator 34 is stopped by the unit 46, thereby fixing the displacement of the roller 32 towards the rollerss 26 and 28, at a value corresponding with the computed suitable deflection of that particular board as a beam between the rollers 26 and 28. It will be appreciated that at this stage, the board is still being held between the pairs of rollers 22 on the table 12, and between the roller 26 and its associated roller 30, and is being loaded cantilever fashion by the roller 32.

However, instead of using the actual thickness of the board to determine what deflection or load should be provided at the first work station 14, it may be more convenient merely to use the nominal thickness of the board to provide a predetermined and fixed deflection in the first work station.

Once the leading edge of the board reaches the roller 28, e.g. at a fixed time interval after it has passed the cell 36.2, the rollers 22 on the table 12 will be caused to release the board. The board will then be gripped between the rollers 26 and 28 on the one hand, and the rollers 30 and 32 on the other hand, and will be stressed as a simple beam over the 500 mm span provided by the rollers 26 and 28, by the roller 32. At this stage, the load transducer associated with the roller 32, in response to the impulse generator associated with the roller 28, starts transmitting force values at 50 mm intervals along the length of the board to the unit 46 for storage and use as described hereunder, the board passing through the work station 14 at a constant deflection determined by the displacement of the roller 32 towards the rollers 26 and 28.

At the same time, in response to the impulse generator 28 the thickness sensor 38 starts to transmit further thickness values to the unit 46. These thickness values are, likewise, transmitted at 50 mm intervals along the length of the board.

When the trailing end of the board reaches the photo-electric cell 36.1, the impulse generator associated with the roller 28 is deactivated, and transmission of thickness and force values by the thickness sensor 38 and the load transducer associated with the roller 32 to the unit 46 is discontinued. The displacement regulator 34 at the same time automatically retracts the roller 32 with its associated load transducer and displacement sensor to their starting position, and according to the preset minimum length of the boards being graded, the appropriate number, e.g. the first two holding rollers 22 on the table 18 are at the same time activated to move the board along the table 18 towards the work station 16. Detection by the photo-electric cell 36.1 of the trailing end of the board likewise releases via the unit 46 an interlock between said cell 36.1 and the table 12, thereby permitting the table 12 to operate again for the succeeding board.

As the board progresses along the table 18, the photoelectric cells 36.3 to 36.10 via the unit 46 activate suitable associated pairs of rollers 22, to keep said board in motion, while deactivating such pairs of rollers 22, upstream of the operative pairs, which are not required. The number of rollers simultaneously activated comprises the two pairs of rollers 22 closest to the leading end of the board. It will be appreciated that activating involves moving the rollers of each pair together to grip the board, while rotating the rollers to move the board, and deactivating the rollers correspondingly involves moving them apart and disconnecting them from the hydraulic drive 47 of the station 14. The V-belt drive of the rollers 22 of the table 18 is, as a safety feature, arranged such that boards cannot move along the table 18 more slowly than they move through the station 14.

While the board is moving along the table 18 the unit 46 computes the highest stiffness value obtained along the length of the board at the work station 14 from the constant deflection of said board and from the highest force reading transmitted by the load transducer. The unit then computes from this highest stiffness value and a pre-programmed safe maximum bending stress, the highest non-destructive stress which the board should be capable of withstanding in the work station 16, together with the displacement of the roller 32 of the station 16 required to produce this stress of the board.

When the leading end of the board reaches the photoelectric cell 36.11 the associated displacement regulator 34 starts moving the roller 32 towards the associated rollers 26 and 28 to achieve this computed displacement. When the leading end of the board reaches the roller 28, as with the station 14, the pulse generator of the associated drive roller 28 is activated. The associated displacement sensor 40 transmits said displacement to the unit 46 and the displacement regulator 34 is stopped when the computed displacement is reached.

When the leading end of the board reaches the roller 28, the remaining operative holding rollers 22 on the table 18 are released, the other holding rollers on the table 18 having previously been released.

The board will once again be loaded at substantially the same positions, spaced 50 mm apart, as it was loaded at in the work station 14, and in this regard it is to be noted that the spacing between the rollers 26, 28 in the station 16 is the same as in the station 14, and that the roller 32 is once again midway between the rollers 26 and 28. The geometry and arrangement of the rollers 26, 28 and 32 is thus the same at the two stations 14 and 16, although the station 16 and its rollers and other parts can be of heavier and more robust construction than those encountered in the station 14, to cater for the higher stresses encountered in the station 16.

When the leading end of the board reaches the roller 28 the load transducer associated with the roller 32 transmits the force values required to load the board to said constant deflection to the unit 46 in response to the pulses generated by the pulse generator associated with the roller 28, the board again being gripped, as in the station 14, between the rollers 26, 28 and the rollers 30, 32 and being loaded as a simple beam by the roller 32 with the rollers 26, 28 as supports.

When the trailing end of the board reaches the photoelectric cell 36.11 said pulse generator is deactivated and the displacement regulator 34 moves the roller 32 with the associated displacement sensor 40 to their starting positions, ready for the next board and the holding rollers 22 on the table 20 are activated to remove the board from the station 16.

It will be appreciated in this regard that while the board is leaving the station 16 and is entering the rollers on the table 20, it will be passing through the printing table 42 across which it is driven by the roller 44.1 in conjunction with the rollers 44.2, 44.11 and 44.21. Before the timber length has left the printing table, the unit 46 will have calculated the grade of the board and other data such as the grades of various sections of the board, the zones of weakness and the zone of greatest weakness of the board, and the like, and such data will be marked on the board.

The unit 46 will be pre-programmed according to statistically sufficient data obtained from boards of the same species or type of wood and of the same nominal dimensions, tested e.g. under laboratory conditions on a simple bending beam apparatus having its supports at the same spacing as rollers 26 and 28, and having a central loading mechanism at the same relative position as the roller 32. Thus predictable qualities of the wood such as stiffness, maximum safe value for non-destructive stressing of a particular species, average knot size, etc. can be determined beforehand. The unit 46 is programmed to perform such calculations as are necessary to grade each board from the data supplied to it by the various sensors in the machine, when the board passes through the machine. When each board has been graded, the data pertaining to it are discarded and its circuits are cleared to deal with the succeeding board.

If desired, the machine can be provided with one or more digital counters, to indicate the total number of boards graded, and the number of boards in each grade. Furthermore, the number of positions on each board corresponding to each different grade can be counted, if necessary.

An advantage of the present invention is that it makes possible the particular method of grading which does not form part of the present invention, wherein, as the board passes through the work station 16 a predetermined number of the highest values of modulus of elasticity (e.g. the five highest) obtained from the data measured at the various positions 50 mm apart are averaged by the unit 46 to obtain the clear modulus of elasticity for the board i.e. that corresponding to the "clear" stiffness of the board defined above. Similarly, the minimum modulus of elasticity for the board is calculated and the board is graded by a formula (not part of the present invention) which takes into account the difference between the clear modulus of elasticity i.e. the clear stiffness of the board, and the minimum modulus of elasticity, i.e. the minimum stiffness of the board, (the higher the difference, the lower being the grade of the board, and the lower the minimum modulus, the lower the grade).

As mentioned above, results obtained from stressing at the first work station are used to determine the highest safe non-destructive stressing to which the board can be subjected in the second station. The modulus of elasticity, i.e. the stiffness of the board, is calculated by known methods from a comparision between the increase in deflection obtained in the second station when compared with the first station, with the increase in load in the second station compared with the first station. This is done for each of the positions at 50 mm spacings along the board for which measurements are taken. In determining the modulus of elasticity, the actual thickness of the board at the exact position where strength is measured is not used by itself, but instead the average value of thickness of the board is used for short distances on either side of said position. Thus the average value of the measured thickness for the, say, five or seven positions straddling the position where load and deflection are measured, can be used for the thickness value, so as to increase accuracy and avoid the effects of local discrepancies in thickness.

Thus the modulus of elasticity is obtained for the board at each of a plurality of positions spaced 50 mm apart along the length of the board, except for those portions of the board at its ends which are too close to said ends to be able to be stressed across the support rollers 26, 28.

These values, allow the clear modulus of elasticity and the minimum modulus of elasticity for the portion of the board where measurements have been taken, to be calculated, as mentioned above.

The applicant has found that an advantage of the invention is that grading of boards according to the formula (not part of the invention):

$$G = 1 - \frac{(\text{clear modulus of elasticity}) \times B}{(\text{minimum modulus of elasticity})}$$

where G = grade of timber

B = experimentally determined constant is made possible, and this gives substantially more accurate grading than prior systems known to the applicant. The improved grading is better in that, because of greater accuracy, substantially fewer boards have to be rejected or assigned to grades which are lower than the actual grade to which they are entitled. The applicant has found that, by using the method of the invention in conjunction with the use of the above formula, the reduction in the number of boards which are incorrectly graded is such as to increase the total value of the boards graded by up to 20%.

The machine described with reference to the drawings has a number of other advantageous features. Thus, during deflection, the boards are deflected laterally, thereby avoiding any influence of gravity on the grading. Furthermore, in determining the final grade of the board, regard is had to data representing incremental deflections and loadings, from a comparison between the original stressing in the first work station 14 and the different stressing in the second work station 16. This is very important in that it eliminates the effect of bow of the boards on the readings, leading to greater accuracy.

A further advantage is that each board is to a certain extent treated individually. Thus the deflection and loading applied in the first work station can, optionally, be tailored to the thickness of the individual board, which thickness is physically measured before the board is loaded, so that the deflection of the board in the first work station 14 is individually set at a suitable value by comparison of the board's thickness and other nominal dimensions with previously collected laboratory data relating stiffness to strength. This is done by means of the cantilever loading in the first work station 14, before the beam bending measurements there.

Then, whether an individually tailored deflection and loading are used in the first work station or, instead, a fixed deflection depending on the nominal thickness of the board is employed, results obtained from the beam bending in the first work station, via the unit 46 are used to determine a suitable individually tailored deflection (and hence stress) for the second work station 16. The deflection and loading in the second work station 16 are set by the unit 46 to be slightly below the maximum safe or non-destructive bending stress which the data from the first work station indicate is capable of being withstood by that particular board. Thus, once the board has passed through the second work station it has in fact been proof-loaded, and inferior boards which do not live up to the prediction are tested to destruction.

An important advantage of the invention is that stressing takes place at closely spaced 50 mm intervals along each board, together with thickness measurements at the same intervals. Accurate average values of thickness and stiffness can thus be obtained, enabling accurate calculations to be made of the modulus of elasticity of the board, used in the grading of the boards. As the thickness of the board is raised to the third power in the calculation of such modulus of elasticity, an accurately measured average value for the thickness of the board is a substantial advantage, leading to more accurate grading.

Furthermore, the number of closely spaced loadings in the first work station 14 permits the stiffness of the board to be measured at a number of positions, and enables lowest and the highest stiffness value of the board to be obtained in the first work station 14 and to be used for calculating the deflection and hence stress to be applied in the second work station. This assists in the non-destructive proof-loading. Thus, the lowest modulus of elasticity and stiffness of the board determine the final grade of the board but the highest modulus of elasticity and stiffness of the board obtained in the first work station are used to determine the final loading in the work station 16, and this loading can be set at a relatively high non-destructive value, thereby to obtain larger, and hence more accurate, differential load readings between the first and second work stations, for the purpose of greater accuracy of grading.

In particular, measuring at closely spaced 50 mm intervals ensures that no significant knot or similar imperfection will escape detection, and its effect on the stiffness of the board will be accurately measured. Thus accurate values for the minimum stiffness and minimum modulus of elasticity of the boards will be obtained.

Because the installation makes use, in the beam bending tests in the stations 14 and 16, of different load measurements at a constant deflection, relatively accurate data can be obtained over the short span of 500 mm between the rollers 26 and 28. This is an advantage in that the first of the series of load readings can take place as soon as the leading end of the board reaches the support roller 28, in the work station in question. The lengths of each board at opposite ends thereof which are thus not loaded and are thus ungraded, can be kept as short as possible, being equal approximately to the span between the rollers 26 and 28. Thus a relatively long proportion at the centre of each board is loaded and hence graded at 50 mm intervals, enabling zones of weakness such as knots or the like to be identified and located, and their effect on the minimum stiffness of the board to be calculated. The exact location of such zones of weakness can be marked on the board by a suitable marking mechanism on the printing table 42, connected to the unit 46, and the unit 46 can be pre-programmed to identify boards at which the zones of weakness are positioned so as to permit economic cross-cutting of such boards to provide shorter sound boards.

As mentioned above, the geometries of the work stations 14 and 16, and particularly the spacings between the rollers 26, 28 and 32 in the longitudinal direction, are identical, thus permiting the loadings at 50 mm spaced intervals in the work station 16 to be performed, within close tolerances, at substantially the same positions as the loadings in the work station 14. This is advantageous for accurately locating zones of weakness and the effect thereof on stiffness and for enabling the indication of different grades of the board at different positions along its length.

An important advantage of the invention is thus that the method permits an accurate value to be obtained for the minimum stiffness of the board, and an accurate value for the clear stiffness of the board, while the method permits these to be used in an accurate formula for grading while ensuring that as much as possible of the length of the board is subjected to measurement, and while no significant imperfections are missed. The method then permits interrelation of these stiffnesses by using the minimum stiffness or minimum modulus of elasticity, together with the independently measured clear stiffness or clear modulus of elasticity, to grade the board, the grade being dependent on both said minimum value and the difference between the minimum value and the independently measured clear value. The values measured can then be related as indicated above, for example by using the minimum stiffness or minimum modulus of elasticity, together with the independently measured clear stiffness or clear modulus of elasticity, to grade the board, the grade being dependent on both said minimum value and said difference.

As the method permits results to be obtained which are more accurate than those previously known to the applicant, a significant saving in incorrectly rejected or incorrectly downgraded timber can be achieved, as the margin of safety required in the grading is reduced. It is the employment of closely spaced measurements (about 50 mm) and reduced spans (about 500 mm) which permit the method to be applied with accuracy. The close spacings in measurements and reduced span give an accurate value for minimum stiffness, and magnify the effect of defects, while measurement of load changes at constant deflections permit accurate measurement at the reduced span employed.

Finally, although it will be appreciated that the marking mechanism can mark the grade of the board at each position at which it is loaded, it is contemplated that the graded central portion of the board will be divided into sections lengthwise, and that each such section will be marked with the minimum grade of that section, which is the minimum stiffness found among the positions along that section where loading took place.

Although the method of the invention has been described with reference to a relatively sophisticated automated apparatus, it will however be appreciated that the invention contemplates also use of simpler apparatus, provided it is capable of performing the steps required by the method. Thus, for example, the pairs of rollers 22.1, 22.2 may be omitted from the infeed and outfeed tables and any other suitable arrangement may be used for infeed and outfeed purposes.

I claim:

1. A method of stress grading timber which comprises:
    continuously moving a length of timber;
    stressing the moving length by applying a transverse load thereto, the length being supported by two supports between which the load is applied and the load causing a deflection of the timber length;
    measuring the load and/or deflection;
    stressing the moving length differently by thereafter applying a different load to the timber length at the same position while supported in the same fashion to obtain a different deflection; and
    measuring the different load and/or the different deflection;
    the timber length being freely supported as a simple beam during each stressing thereof so that it is substantially unconstrained during the stressing except by the load and the two supports between which the load is applied, the original load and the original deflection being related to the different load and different deflection according to predetermined criteria, thereby to grade the timber length.

2. A method as claimed in claim 1, in which the original load and the different load are applied from the same side of the timber length, so that the length is in each case deflected in the same direction.

3. A method as claimed in claim 1, in which the original and different loads are applied to the length of timber at a plurality of spaced positions spaced lengthwise along the timber length.

4. A method as claimed in claim 1, in which the span between each pair of supports between which the length is loaded is less than 600 mm.

5. A method as claimed in claim 1, in which each original load is applied at one location, the length being moved to another location where each different load is applied.

6. A method as claimed claim 1, in which the thickness of the length is measured, and is used in conjunction with the loads and deflections, to grade the length.

7. A method as claimed in claim 1, in which the deflection obtained from each original stressing is used to predict a suitable non-destructive load to which the length is to be subjected during the corresponding different stressing.

8. A timber stress grading machine which comprises:
    means for continuously moving a length of timber;
    means for stressing the moving length by applying a transverse load thereto, the length being supported by two supports between which the load is applied, to cause a deflection of the timber length;
    means for measuring said load and/or deflection;
    means for then stressing the moving length differently at the same position while supported in the same fashion to obtain a different deflection;
    means for measuring the different load and/or the different deflection; and
    means for relating the original load and original deflection to said different load and different deflection according to predetermined criteria, thereby to grade the timber length, the supports in each case acting freely to support the length as a simple beam during stressing thereof, so that the length is substantially unconstrained during stressing except by the load and the two supports between which the load is applied.

9. A machine as claimed in claim 8, in which the means for applying the original load and the different load to the timber length are arranged to act on the same side of the timber length, so that the length is in each case deflected in the same direction.

10. A machine as claimed in claim 8, which is adapted to apply the original load and the different load to the length of timber at a plurality of spaced positions, spaced lengthwise along the timber length.

11. A machine as claimed in claim 8, in which the span between each pair of supports between which the length is loaded is less than 600 mm.

12. A machine as claimed in claim 8, in which the means for originally stressing the timber length is at one location, the means for differently stressing the length being at a different location and the machine including means for moving the timber length from the one location to the different location.

13. A machine as claimed in claim 8, which includes means for measuring the thickness of the timber length, the means for relating the original load and deflection to the different load and deflection being adapted to use the thickness measurement(s) so obtained, in the grading of the timber length.

14. A machine as claimed in claim 8, in which the means for stressing the timber length differently is responsive to the load and deflection of the original stressing, and is adapted to provide said different load with a magnitude which depends on said original load and deflection.

* * * * *